United States Patent [19]
Davis

[11] Patent Number: 4,516,974
[45] Date of Patent: May 14, 1985

[54] UNIVERSAL VENT DEVICE AND METHOD FOR OSTOMY APPLIANCES

[75] Inventor: Jeffrey J. Davis, New Lebanon, Ohio

[73] Assignee: Imnetec Inc., Vandalia, Ohio

[21] Appl. No.: 449,455

[22] Filed: Dec. 13, 1982

[51] Int. Cl.³ .............................................. A61F 5/44
[52] U.S. Cl. ................................. 604/333; 55/385 C
[58] Field of Search ............ 55/385 C, DIG. 13, 503, 55/505; 604/317, 332–337, 345, 359

[56] References Cited

U.S. PATENT DOCUMENTS

| | | | |
|---|---|---|---|
| 2,555,086 | 5/1951 | Guinn | 128/283 |
| 3,952,727 | 4/1976 | Nolan | 128/283 |
| 4,203,445 | 5/1980 | Jessup et al. | 128/283 |
| 4,268,286 | 5/1981 | Steer et al. | 604/333 |
| 4,318,406 | 3/1982 | McLeod | 128/283 |
| 4,386,930 | 6/1983 | Cianci | 604/317 |
| 4,411,659 | 10/1983 | Jensen et al. | 604/332 |
| 4,451,258 | 5/1984 | Jensen | 604/333 |

FOREIGN PATENT DOCUMENTS 2094153  9/1982  United Kingdom ............... 604/333

*Primary Examiner*—C. Fred Rosenbaum
*Assistant Examiner*—J. L. Kruter
*Attorney, Agent, or Firm*—Jacox & Meckstroth

[57] ABSTRACT

A universal vent device for the pouch of an ostomy appliance. The vent device is attachable to any pouch which has an enclosure wall of relatively thin pliable plastics material or the like. The vent device comprises a housing member for a gas-permeable, liquid absorbent filter element. The housing member has a vent opening leading outwardly therefrom. A connector member is adapted to attach the housing member to the enclosure wall. The connector member is movable into the pouch and has a stem adapted to extend through the enclosure wall. The stem attaches to the housing. The stem has a passage therethrough for communication between the interior of the pouch and the interior of the housing, for flow of gases from the pouch into the housing member. The stem also serves as a conductor of fluids into the pouch for cleaning and deodorizing the pouch.

25 Claims, 6 Drawing Figures

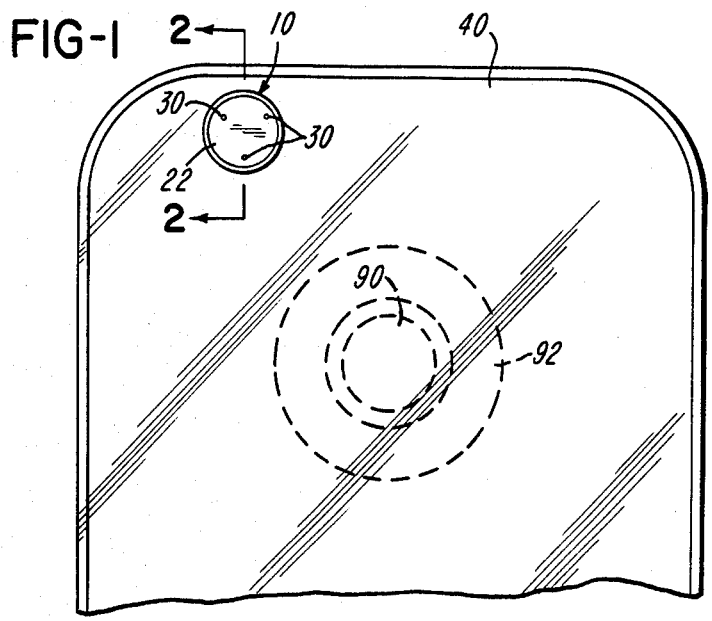
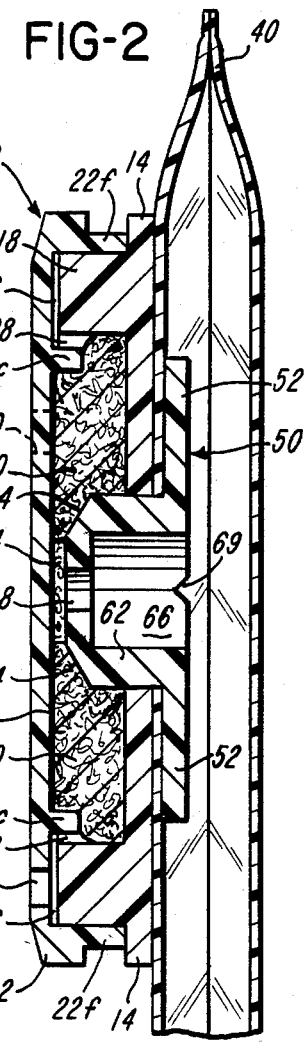
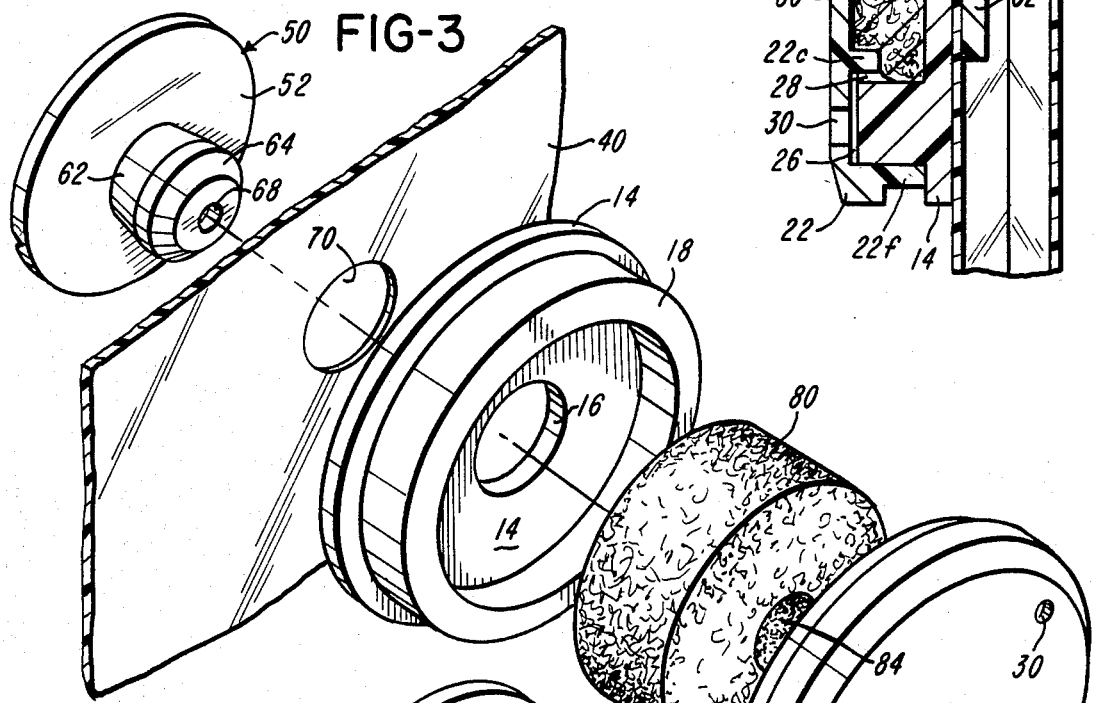
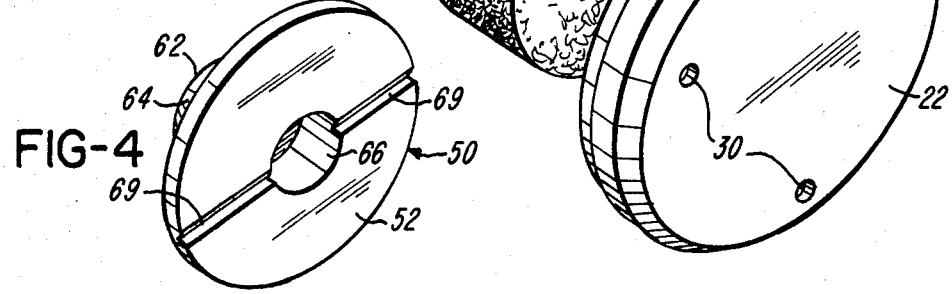

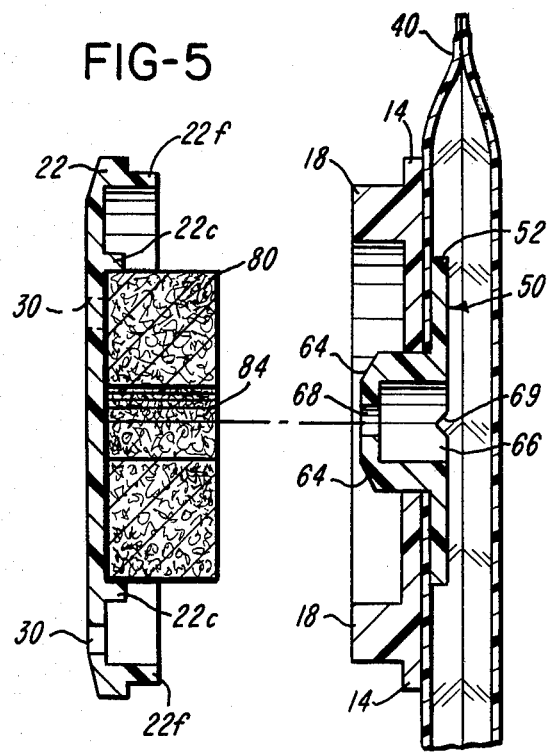
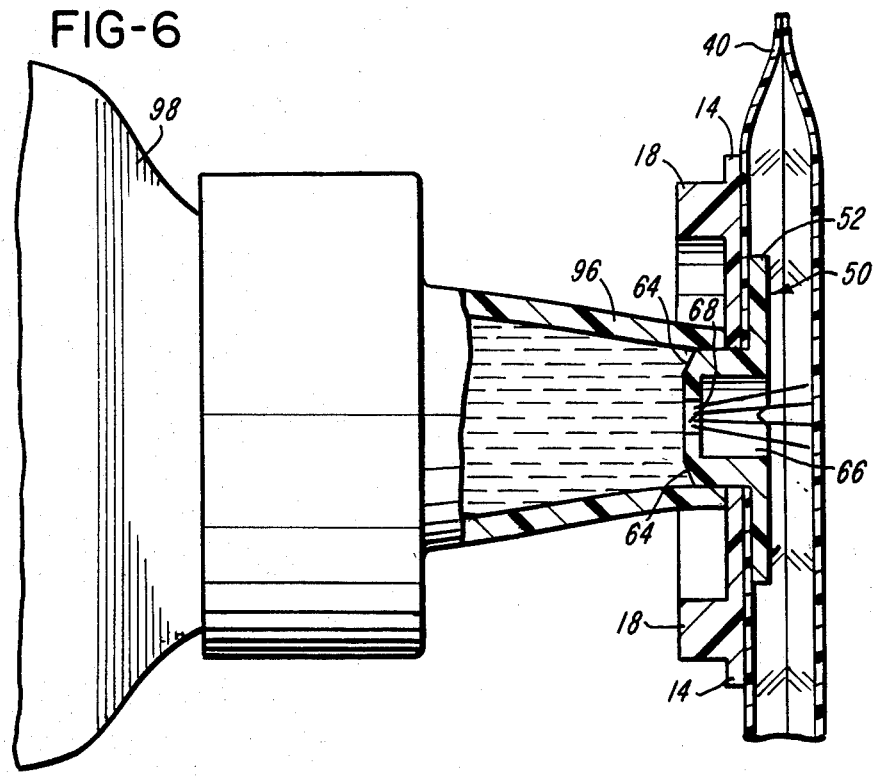

UNIVERSAL VENT DEVICE AND METHOD FOR OSTOMY APPLIANCES

BACKGROUND OF THE INVENTION

Ostomy surgery is found necessary for many people. There are two kinds of ostomy surgery related to the device of this invention: colostomy (partial removal of the large intestine) and ileostomy (removal of the entire large intestine). After each type of surgery is performed, some type of artificial appliance must be worn by the patient. Most of such appliances comprise a pouch of a plastics material, the pouch having a receiver passage portion adhesively attached to an abdominal portion of the body immediately encompassing an opening in the body to receive waste materials from the abdominal portion.

The waste materials include solids and semi-liquids. Also intestinal gases flow into the pouch. If means are not provided to vent the gases from the pouch, a ballooning action occurs in the pouch. Such ballooning is, of course, objectionable with regard to the comfort and appearance of the patient. There have been numerous attempts to construct a satisfactory gas venting device which may remove odors from the gases flowing into the pouch. For example, U.S. Pat. Nos. 2,555,086, 3,952,727, 4,203,445, and 4,318,406 relate to means for venting gases from an ostomy appliance.

Known vent devices for ostomy appliances have two major limitations: they readily clog and prevent passage of gases from the appliance and/or they are designed specifically for a particular appliance and cannot be used with other appliances.

Most ostomy appliance pouches are not readily cleanable and/or serviceable.

It is therefore an object of this invention to provide a gas vent device for ostomy appliances which device is readily mountable upon any plastics pouch type of ostomy appliance, does not readily clog, is cleanable and reusable, while providing a high degree of reliability against leakage, odor, and spotting.

Another object of this invention is to provide such a gas vent device through which fluid can be easily introduced into the pouch for cleaning and for deodorization of the pouch.

Other objects and advantages of this invention reside in the construction of parts, the combinations thereof, the method of production, and the mode of use, as will become more apparent from the following description.

BRIEF DESCRIPTION OF THE INVENTION

A universal vent device of this invention comprises a substantially flat housing which includes a base portion, a wall portion, and a cover portion. The base portion of the housing is adapted to be positioned in engagement with the outer surface of a pouch, preferably at the upper part of the pouch. The base portion of the housing has an opening therethrough, leading to the interior of the housing. The cover portion is removably attachable to the wall portion of the housing.

A vent device of this invention also comprises a connector member, including a stem member which is adapted to be forced from the inside of the pouch through the wall of the pouch, as the stem die-cuts an opening through the wall of the pouch. The stem snap-fits into the opening in the base portion of the housing to attach the stem to the base portion of the housing. The stem extends from a base portion or disc portion of the connector member which is positioned within the pouch. The base portion of the connector member engages the interior surface of the wall of the pouch, as the base portion of the housing engages the exterior surface of the wall of the pouch. Thus, a small portion of the upper part of the wall of the pouch is clamped between the base portion of the connector member and the base portion of the housing, as the stem extends through the wall of the pouch. Thus, the housing and the connector member are removably attached to the wall of the pouch.

The stem has a passage therethrough for communication between the interior of the pouch and the interior of the housing. A gas permeable, liquid absorbing foam sponge filter element encompasses the stem within the housing and substantially fills the housing. The base portion of the housing has a cylindrical wall portion extending therefrom, and the cover portion of the housing snaps onto the cylindrical wall portion to enclose the housing. The cover portion of the housing has one or more vent passages therethrough.

BRIEF DESCRIPTION OF THE VIEWS OF THE DRAWING

FIG. 1 is a fragmentary elevational view of a portion of a pouch of an ostomy appliance. This view also shows a vent device of this invention attached to the pouch.

FIG. 2 is a greatly enlarged sectional view, taken substantially on line 2—2 of FIG. 1.

FIG. 3 is an exploded perspective view, illustrating a vent device of this invention and showing a fragment of the pouch to which the vent device is attached, and drawn on substantially the same scale as FIG. 2.

FIG. 4 is a perspective view of a connector member of a device of this invention.

FIG. 5 is a fragmentary sectional view similar to FIG. 2, drawn on a smaller scale, and showing the cover portion of the housing removed therefrom.

FIG. 6 is a diagrammatic sectional view illustrating a method by which a vent device also serves as a fluid conductor for introducing fluids into the pouch.

DETAILED DESCRIPTION OF THE INVENTION

A vent device of this invention comprises a housing 10 having a base 14. The base 14 has an opening 16 therethrough, as illustrated in FIG. 3. Integral with the base 14 is a cylindrical wall 18. The housing 10 includes a cover member 22 which has an outer flange part 22f which snugly and resiliently encompasses the cylindrical wall 18 and preferably engages the base 14, to position the cover member 22 with respect to the base 14. A small annular passage 26 is provided between the end of the cylindrical wall 18 and the cover member 22. The cover member 22 is provided with one or more vent passages 30 leading from the annular passage 26. The cover member 22 is also provided with an inner cylindrical collar 22c which is spaced slightly from the cylindrical wall 18 to provide a passage 28 leading to the passage 26, as shown in FIG. 2.

The housing 10 is adapted to be positioned on the exterior surface of the upper portion of an ostomy appliance pouch, such as a pouch 40, ordinarily of a plastics material, shown in fragment in FIGS. 1, 2, 3, 5, and 6. In mounting the housing 10 upon the exterior surface of the upper portion of the pouch 40, a connector member 50 is inserted into the pouch 40 through an opening (not shown) therein, usually at the lower portion of the pouch 40. The connector member 50 is moved to the upper portion of the pouch 40. The connector member 50 comprises a base or disc 52, from which a protuberance or stem 62 extends at the central portion thereof. The stem 62 has a relatively large passage 66, leading to a relatively small passage 68 at the end of the stem 62. The outer surface of the base or disc 52 has a diametrically extending groove 69 leading to the passage 66. The end of the stem 62 has an annular tapered cutter portion 64.

In attaching the housing to an enclosure wall of the pouch 40 the cutter portion 64 of, the stem 62 is forced through an enclosure wall of the pouch 40 at the upper part thereof. In this manner, the stem 62 in a die-cutting action forms a hole 70 in the enclosure wall of the pouch 40, as illustrated in FIG. 3, and the stem 62 extends through the hole 70, shown in FIG. 2. The term "die-cutting action" includes piercing action or any other type of cutting action by which the hole 70 is formed.

After the stem 62 is forced through the enclosure wall of the pouch 40 to form the hole 70, the housing 10 is positioned at the exterior surface of the enclosure wall of the pouch 40. Then the base 14 of the housing 10 is forced upon the stem 62, as the stem 62 extends through the opening 16 in the base 14. Preferably, the stem 62 decreases slightly from a larger dimension to a smaller dimension from the end of the stem 62 toward the base 52 of the connector member 50, as best illustrated in FIG. 3. Therefore, as the stem 62 is attached to the base 14, there is a resilient snap type of connection between the base 14 and the stem 62. Thus, the base 14 of the housing 10 and the stem 62 of the connector member 50 are firmly attached together, and a part of the wall of the pouch 40 is clamped between the base 14 of the housing 10 and the base 52 of the connector member 50. A vent device of this invention is thus secured to the pouch 40. Preferably, the housing 10 and the connector member 50 are made of a relatively light weight plastics material, such as nylon, or the like.

Positioned within the housing 10 is a gas permeable, liquid absorbant foam sponge or cellular sponge member 80, which has an opening 84 therethrough, slightly smaller than the greatest diameter of the stem 62, thus permitting the sponge 80 to snugly encompass the stem 62. The sponge 80 is normally slightly larger than the space provided within the housing 10. Therefore, the sponge 80 is slightly compressed within the housing 10. The sponge 80 is preferably attached to the inner surface of the cover 22, as shown in FIG. 5, by an adhesive 82, shown in FIG. 2. Therefore, the sponge 80 is positioned within the housing 10 when the cover 22 is attached to the housing 10.

In FIG. 1 a stoma opening 90 in the pouch 40 is illustrated. The opening 90 encompasses an annular adhesive surface element 92 on the exterior of the pouch 40 for attaching the pouch 40 to the body of the wearer. Material discharged from the patient's body thus travels into the pouch 40 through the opening 90.

Gases which flow into the pouch 40 through the opening 90 travel upwardly within the pouch 40 and enter the passage 66 in the stem 62. Odors in the gases are removed by a deodorant which is introduced into the interior of the pouch 40 in a manner discussed below. If the pouch 40 should be substantially empty, and if the surface of the base 52, opposite the stem 62, should be in engagement with the inner surface of the pouch 40, the gases travel through the groove 69, and then into the passage 66. If the stem 62 is not in engagement with the opposite enclosing wall of the pouch 40, the gases travel directly into the passage 66. The gases travel through the larger passage 66 and through the smaller passage 68 and into the housing 10. The gases then travel through the cellular foam sponge member 80. The gases then travel through the passages 28 and 26 and flow outwardly through one or more of the vent passages 30.

The passage 66 in the stem 62 serves as a moisture trap when solids and semi-liquid materials within the pouch 40 move into the passage 66. Thus, moisture and materials other than gases do not readily travel through the passage 68 into the housing 10. If moisture travels into the housing 10, most of such moisture moves along the tapered portion 64 at the end of the stem 62 rather than flowing directly into the sponge 80. Thus, passages for gases to flow through open cells in the sponge 80 are maintained. When a greater amount of moisture enters the housing 10, the sponge 80 absorbs the moisture, and when the moisture is not excessive, the sponge 80 permits gases to flow through the sponge 80.

The inner collar 22c of the cover 22 serves as a barrier to maintain portions of the outer part of the sponge 80 away from the cylindrical wall 18, to maintain the passage 28 free from the sponge 80, for flow of gases through the passage 28.

For best operation, the area of the passage 68 should be such that free flow therethrough is permitted, but the area should be sufficiently small to prevent an excessive rate of flow therethrough.

In regard to this invention, liquid deodorant is introduced into the pouch 40 for deodorizing the gases and the material within the pouch. This invention provides means by which a liquid can be easily and readily introduced into the pouch 40. As illustrated in FIG. 5, the cover 22 and the sponge 80, attached thereto, are easily removed as a unit. As illustrated in FIG. 6, with the cover 22 and the sponge 80 removed from the base 14 of the housing 10, a nozzle 96 of a liquid container 98 is placed into covering engagement with the outer surface of the stem 62, which is adapted to receive the nozzle 96. Then liquid is forced through the passages 68 and 66 and into the pouch 40, as illustrated in FIG. 6. In this manner, a liquid deodorant can be introduced into the pouch 40 for deodorization thereof, or a liquid can be introduced into the pouch 40 for cleaning the interior thereof.

To clean a device of this invention, the cover 22 and the sponge 80 are removed, as illustrated in FIG. 5. The sponge 80 is cleaned and dried with a suitable cloth or the like. Fresh deodorant is injected into the pouch through the stem 62, and the cover 22 with the sponge 80, is replaced to positions shown in FIG. 2.

Thus, it is understood that a vent device of this invention is easily and readily attached or mounted to any conventional pouch of an ostomy appliance. The vent device permits the gases to flow outwardly from the pouch, while preventing the flow of moisture and other materials from the pouch. The vent device of this invention provides means by which a liquid is easily introduced into the pouch for deodorizing and cleaning the interior of the pouch.

Although the preferred embodiment of the ostomy vent device and method of this invention has been described. it will be understood that within the purview of this invention various changes may be made in the form, details, proportion and arrangement of parts, the combination thereof, and the mode of use, which generally stated consist in a structure and method within the scope of the appended claims.

The invention having thus been described, the following is claimed:

1. A universal vent device for attachment to a pouch of an ostomy appliance, the pouch having an enclosure wall, comprising:

a housing including a base provided with a cylindrical wall, the base of the housing having an opening therethrough, a cover member having a cylindrical flange tightly encompassing and removably attached to the cylindrical wall, the cover member having a vent opening therethrough, a connector member provided with a base and stem means extending from the base, the stem means having a cutter part, the stem means having a passage therethrough, the base of the connector member being within the pouch with the stem means cutting the enclosure wall of the pouch in a die-cutting action and extending through the enclosure wall of the pouch, the housing being on the exterior surface of the enclosure wall of the pouch, the stem means snugly extending through the opening in the base of the housing and attaching the connector member to the base of the housing, the part of the enclosure wall of the pouch which encompasses the opening in the enclosure wall thus being clamped between the base of the housing and the base of the connector member, a portion of the stem means being within the housing, and a gas permeable filter element encompassing the stem means within the housing, gases within the pouch traveling from the pouch through the passage within the stem means, then through the gas permeable filter element in the housing and outwardly from the housing through the vent opening in the cover member, the cover member being readily removable from the cylindrical wall to permit access to the gas permeable filter element for replacement thereof.

2. The vent device of claim 1 in which the gas permeable filter element is attached to the cover member and movable therewith.

3. The vent device of claim 1 in which the cover member includes an annular inner collar spaced from the cylindrical wall and forming a gas passage between the cylindrical wall and the annular inner collar.

4. The vent device of claim 1 in which there are a plurality of vent openings in the cover member adjacent the periphery thereof.

5. The vent device of claim 1 in which the cover member has an inner surface spaced from the cylindrical wall and forming a gas passage between the inner surface of the cover member and the cylindrical wall, there being a vent opening in the cover member in communication with said gas passage.

6. A universal vent device for attachment to a pouch of an ostomy appliance, the pouch having an enclosure wall, comprising:

a housing including a base provided with a cylindrical wall, the base of the housing having an opening therethrough, a cover member having a cylindrical flange tightly encompassing and removably attached to the cylindrical wall, the cover member having a vent opening therethrough, a connector member provided with a base and a stem extending from the base, the stem having a passage therethrough, the stem having a cutter part, the base of the connector member being within the pouch with the stem cutting through the enclosure wall in a die-cutting action and extending through the enclosure wall of the pouch, the housing being on the exterior surface of the enclosure wall of the pouch, the stem snugly extending through the opening in the base of the housing and attaching the connector member to the base of the housing, the part of the enclosure wall of the pouch which encompasses the opening in the enclosure wall thus being clamped between the base of the housing and the base of the connector member, a portion of the stem being within the housing, and a gas permeable filter element encompassing the stem within the housing, gases within the pouch traveling from the pouch through the passage within the stem, then through the gas permeable filter element in the housing and outwardly from the housing through the vent opening in the cover member, the stem of the connector member having a receiver portion which is adapted to receive a part of a liquid introduction member for introducing liquids into the pouch through the stem for deodorizing the pouch and for cleaning the interior of the pouch.

7. A universal vent device for attachment to a pouch of an ostomy appliance, the pouch having an enclosure wall, comprising a housing which includes a base provided with an opening therethrough leading to the interior of the housing, the housing also having a vent opening leading from the interior of the housing to the exterior of the housing, a connector member having a portion adapted to be positioned within the pouch and in engagement with the interior surface of an enclosure wall of the pouch, the connector member including a base and a stem extending from the base, the stem means having a cutter part and being adapted to cut the enclosure wall and in a die cutting action to extend through the enclosure wall of the pouch, the stem means being snugly positioned in the opening in the base of the housing and attaching the connector member to the housing, with a portion of the enclosure wall which encompasses the opening clamped between the base of the connector member and the base of the housing, gases within the pouch traveling through the passage in the stem means and into the housing, the gases then traveling outwardly from the housing through the vent opening in the housing.

8. The vent device of claim 1 in which the housing includes a removable cover member and in which the vent opening extends through the cover member.

9. The vent device of claim 7 in which the stem has an end portion within the housing and in which the end portion of the stem is tapered and a porous sponge encompasses the stem, and the tapered end portion of the stem directing moisture to travel along the stem.

10. The vent device of claim 7 in which the housing includes an exterior wall and which also includes an annular collar within the housing and spaced from the exterior wall, the collar also being spaced from the stem, a porous sponge member encompassing the stem and engaging the collar, the housing having a vent passage adjacent the exterior wall, the collar and the exterior wall forming a passage leading to the vent passage for flow of gases from the housing through the vent passage.

11. The vent device of claim 7 in which the housing includes a cover member and in which the housing has a cylindrical wall snugly encompassed by a portion of the cover member and attaching the cover member to the housing, the cover member having a portion engaging the base of the housing and positioning the cover member with respect to the base.

12. The method of venting a pouch of an ostomy appliance, the pouch having an enclosure wall, comprising: positioning a connector member within the pouch, the connector member having a base portion and a stem portion, the stem portion having a cutter part, the stem portion also having a passage therethrough, forcing the cutter part of the stem portion of the connector member through the enclosure wall in a die-cut action to form an aperture through the enclosure wall with the stem portion extending through the enclosure wall.

13. The method of venting a pouch of an ostomy appliance, the pouch having an enclosure wall, comprising: positioning a connector member within the pouch, the connector member having a base portion and a stem portion, the stem portion having a cutter part, the stem portion also having a passage therethrough, forcing the stem portion of the connector member through the enclosure wall in a die-cut action to form an aperture through the enclosure wall as the stem portion extends through the enclosure wall, attaching a housing to the stem on the exterior of the enclosure wall of the pouch, the housing having a vent opening therethrough, gases within the pouch thus being permitted to travel from the pouch through the passage in the stem, and through the housing and outwardly from the housing through the vent opening therein.

14. The method of venting a pouch of an ostomy appliance, the pouch having an enclosure wall, comprising: positioning a connector member within the pouch, the connector member having a base portion and a stem portion, the stem portion having a cutter part, the stem portion also having a passage therethrough, forcing the stem portion of the connector member through the enclosure wall in a die-cut action to form an aperture through the enclosure wall as the stem portion extends through the enclosure wall, attaching a housing to the stem on the exterior of the enclosure wall of the pouch, the housing having a vent opening therethrough, positioning a gas permeable liquid absorbant filter element within the housing, gases within the pouch thus being permitted to travel from the pouch through the passage in the stem and through the filter element, through the housing and outwardly from the housing through the vent opening therein.

15. A universal vent device for a pouch of an ostomy appliance, the pouch having an enclosure wall, a connector member movable into the interior of the pouch and having a protuberant portion provided with a cutter part, the cutter part of the protuberant portion being adapted to be forced through the enclosure wall to form an aperture through the enclosure wall, with the protuberant portion extending through the enclosure wall, the protuberant portion of the connector member having a passage therethrough leading from the interior of the pouch, a housing on the exterior surface of the enclosure wall, the housing having an interior part, the housing being joined to the protuberant portion of the connector member with the passage of the protuberant portion in communication with the interior part of the housing, the housing having a vent opening, filter means within the housing, the filter means permitting passage of gas therethrough but restraining liquid from passage therethrough, gases within the pouch thus passing outwardly therefrom through the passage in the protuberant portion of the connector member and into the housing, the gases then passing through the filter means and through the housing and outwardly from the housing through the vent opening.

16. The vent device of claim 15 in which the protuberant portion of the connector member is provided with a liquid dispenser connection part for connection with a liquid dispenser for introducing liquid into the interior of the pouch through the protuberant portion of the connector member for cleaning and deodorizing the interior of the pouch.

17. A universal vent device for a pouch of an ostomy appliance provided with an enclosure wall, comprising:
connector means extending through the enclosure wall of the pouch, the connector means being provided with a passage therethrough for fluid communication between the interior and exterior of the pouch, the connector means being provided with a receiver portion for receipt of a portion of a fluid dispenser for introducing fluids into the pouch through the connector means for cleaning and deodorizing the interior of the pouch, the connector means having a cutter part, the connector means being adapted to be forced through the enclosure wall in a die-cut action to form an opening through the enclosure wall through which the connector means extends.

18. The vent device of claim 17 which includes enclosure means attached to the connector means, gas permeable liquid absorbant filter element within the enclosure means, the enclosure means being provided with a vent opening for flow of gases therefrom as gases travel from the pouch into the enclosure means, through the filter means, and outwardly from the enclosure means through the vent opening.

19. A universal vent device for attachment to a pouch of an ostomy appliance, the pouch having an enclosure wall, comprising a housing which includes a base provided with an opening therethrough leading to the interior of the housing, the housing also having a vent opening leading from the interior of the housing to the exterior of the housing, a connector member having a portion adapted to be positioned within the pouch and in engagement with the interior surface of an enclosure wall of the pouch, the connector member including a base and a stem extending from the base, the stem having a cutter part and being adapted to cut through the enclosure wall in a die-cutting action and to extend through the enclosure wall of the pouch and to be snugly positioned in the opening in the base of the housing and attaching the connector member to the housing, with a portion of the enclosure wall clamped between the base of the connector member and the base of the housing, gases within the pouch traveling through the passage in the stem means and into the housing, the gases then traveling outwardly from the housing through the vent opening in the housing, the stem means having a gradually increasing dimension extending from the base of the connector member toward the end of the stem means so that the stem is firmly attached to the base of the housing.

20. A universal vent device for attachment to a pouch of an ostomy appliance, the pouch having an enclosure wall, comprising a housing which includes a base provided with an opening therethrough leading to the interior of the housing, the housing also having a vent opening leading from the interior of the housing to the exterior of the housing, a connector member having a portion adapted to be positioned within the pouch and in engagement with the interior surface of an enclosure wall of the pouch, the connector member including a base and a stem extending from the base, the stem means having a cutter part and being adapted to cut through the enclosure wall in a die-cutting action and to extend through the enclosure wall of the pouch and to be snugly positioned in the opening in the base of the housing and attaching the connector member to the housing, with a portion of the enclosure wall clamped between the base of the connector member and the base of the housing, gases within the pouch traveling through the passage in the stem means and into the housing, the gases then traveling outwardly from the housing through the vent opening in the housing, the housing including a cylindrical wall extending from the base of the housing, the housing also including a cover member having a portion snugly engaging the cylindrical wall and attached to the cylindrical wall, the cylindrical wall having an annular end portion, the cover member having a part engaging the base of the housing to position the cover member with respect to the annular end portion of the cylindrical wall to form a space between the annular end portion and the cover member, the cover member having a vent opening in the portion thereof adjacent the end of the annular end portion of the cylindrical wall, the space between the annular end portion and the cover member forming a passage in the housing leading to the vent opening.

21. A universal vent device for attachment to a pouch of an ostomy appliance, the pouch having an enclosure wall, comprising a housing which includes a base provided with an opening therethrough leading to the interior of the housing, the housing also having a vent opening leading from the interior of the housing to the exterior of the housing, a connector member having a portion adapted to be positioned within the pouch and in engagement with the interior surface of an enclosure wall of the pouch, the connector member including a base and a stem means extending from the base, the stem having a cutter part and being adapted to cut through the enclosure wall in a die-cutting action and to extend through the enclosure wall of the pouch and to be snugly positioned in the opening in the base of the housing and attaching the connector member to the housing, with a portion of the enclosure wall clamped between the base of the connector member and the base of the housing, gases within the pouch traveling through the passage in the stem means and into the housing, the gases then traveling outwardly from the housing through the vent opening in the housing, the stem means having a receiver portion which is adapted to receive a part of a liquid introduction member for introducing liquid into the pouch through the stem means for cleaning and deodorizing the interior of the pouch.

22. The method of venting a pouch of an ostomy appliance, the pouch having an enclosure wall, comprising: positioning a connector member within the pouch, the connector member being provided with a cutter part, forcing the connector member through the enclosure wall and cutting through the enclosure wall in a die-cutting action to form an aperture in the enclosure wall, as the connector member extends through the aperture in the enclosure wall to the exterior of the pouch, attaching a housing to the connector member on the exterior of the pouch, positioning a gas permeable liquid absorbant filter element within the housing, and attaching a cover member to the housing to enclose the housing.

23. The method of venting a pouch of an ostomy appliance, the pouch having an enclosure wall, comprising: positioning a connector member within the pouch, the connector member having a hollow stem provided with a cutter part, forcing the stem through the enclosure wall in a die-cutting action so that the stem extends through the aperture in the enclosure wall to the exterior of the pouch, attaching a housing to the stem of the connector member on the exterior of the pouch in which the housing has a vent opening, positioning a gas permeable liquid absorbant filter element within the housing, and attaching a cover member to the housing to enclose the housing, and injecting a deodorant into the pouch through the hollow stem.

24. The vent device of claim 7 in which the housing includes a removable cover member which when removed provides access to the stem within the housing.

25. The method of venting a pouch of an ostomy appliance, the pouch having an enclosure wall, comprising: positioning a connector member within the pouch, the connector member having a hollow stem provided with a cutter part, forcing the stem through the enclosure wall in a die-cutting action to form an aperture with the stem extending through the aperture in the enclosure wall to the exterior of the pouch, attaching a housing to the stem of the connector member on the exterior of the pouch, positioning a gas permeable liquid absorbant filter element within the housing, and attaching a cover member to the housing to enclose the housing.

* * * * *

UNITED STATES PATENT AND TRADEMARK OFFICE
CERTIFICATE OF CORRECTION

PATENT NO. : 4,516,974
DATED : May 14, 1985
INVENTOR(S) : Jeffrey J. Davis

It is certified that error appears in the above-identified patent and that said Letters Patent are hereby corrected as shown below:

Column 3, line 14, after "40" insert a comma; after "of" delete the comma.

Column 6, line 37, following "stem", first occurrence, insert ---means---.

Column 6, line 39, after "wall" delete "and"; same line, following "action" insert ---and---.

Column 6, line 50, change "1" to ---7---.

Column 8, line 49, following "stem", each occurrence, insert ---means---.

Column 9, line 7, following "stem", first occurrence, insert ---means---.

Column 9, line 43, following "stem", second occurrence, insert ---means---.

Signed and Sealed this

Thirteenth Day of August 1985

[SEAL]

Attest:

DONALD J. QUIGG

Attesting Officer      Acting Commissioner of Patents and Trademarks